United States Patent [19]

Albert et al.

[11] Patent Number: 4,923,866
[45] Date of Patent: May 8, 1990

[54] FUNGICIDAL COMPOSITIONS

[75] Inventors: Guido Albert, Hackenheim; Jürgen Curtze, Geisenheim-Johannisberg, both of Fed. Rep. of Germany

[73] Assignee: Shell Agrar GMBH & Co., KG, Ingelheim am Rhein, France

[21] Appl. No.: 149,516

[22] Filed: Jan. 28, 1988

[30] Foreign Application Priority Data

Jan. 30, 1987 [DE] Fed. Rep. of Germany ....... 3702769

[51] Int. Cl.$^5$ .................... A01N 43/84; A01N 43/86; A01N 43/88; A01N 47/10
[52] U.S. Cl. ................................ 514/237.5; 514/403; 514/491
[58] Field of Search ................ 514/234.2, 228.8, 491, 514/483; 518/237.5

[56] References Cited

U.S. PATENT DOCUMENTS 4,753,934  6/1988  Nickl et al. ....................... 514/231.5

FOREIGN PATENT DOCUMENTS 120321  10/1984  European Pat. Off. .
208999  1/1987  European Pat. Off. .
219756  4/1987  European Pat. Off. .

Primary Examiner—Douglas W. Robinson
Assistant Examiner—Raymond J. Henley, III

[57] ABSTRACT

The invention provides a fungicidal composition comprising at least one systemic, contact and/or soil fungicide and at least one acrylic acid morpholide derivative of the general formula

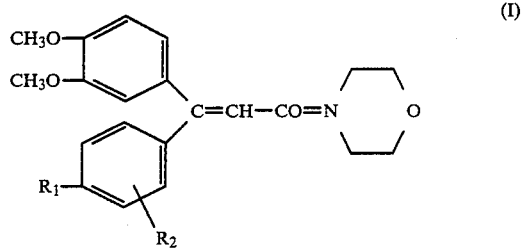

(I)

in which $R_1$ represents a hydrogen, chlorine or bromine atom, a trifluoromethyl, trifluoromethoxy, $C_3$–$C_7$ alkyl, $C_3$–$C_5$ alkoxy, $C_3$–$C_6$ alkenyl, HClFC—$CF_2O$—, HClC=CClO—, cyclohexyl, cyclopentenyl, cyclohexenyl, phenyl, 4-chlorophenyl, 4-ethylphenyl, 4-chlorobenzyl or 4-chlorophenylthio group or a phenoxy group optionally substituted by one or more substituents selected from fluorine and chlorine atoms and methyl and ethoxycarbonyl groups and $R_2$ represents a hydrogen atom, or $R_1$ represents a hydrogen atom and $R_2$ represents a 3-phenoxy group.

9 Claims, No Drawings

FUNGICIDAL COMPOSITIONS

This invention relates to fungicidal compositions comprising combinations of fungicidal substances and, in particular, to the preparation and use of compositions comprising certain acrylic acid morpholide derivatives in combination with certain systemic, contact and/or soil fungicides.

Many different compounds are known for use as systemic, contact or soil fungicides. Examples of some such compounds which are available commercially can be found in "The Pesticide Manual", Eighth Edition, 1987, edited by Charles R. Worthing and S. Barrie Walker, published by The British Crop Protection Council.

It is also known that certain acrylic acid morpholide derivatives are effective in combating a variety of phytopathogenic fungi. Examples of such compounds are disclosed in EP-A1-0 120 321 and EP-A1-0 219 756.

It has now been discovered that the fungicidal effect of some of these acrylic acid morpholides can be improved to a surprising extent if they are used in combination with certain systemic, contact and/or soil fungicides.

According to the present invention there is therefore provided a fungicidal composition comprising at least one systemic, contact and/or soil fungicide and at least one acrylic acid morpholide derivative of the general formula

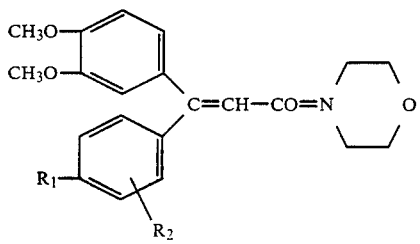

(I)

in which $R_1$ represents a hydrogen, chlorine or bromine atom, a trifluoromethyl, trifluoromethoxy, $C_3$–$C_7$ alkyl, $C_3$–$C_5$ alkoxy, $C_3$–$C_6$ alkenyl, HClFC—$CF_2O$—, HClC=CClO—, cyclohexyl, cyclopentenyl, cyclohexenyl, phenyl, 4-chlorophenyl, 4-ethylphenyl, 4-chlorobenzyl or 4-chlorophenylthio group or a phenoxy group optionally substituted by one or more substituents selected from fluorine and chlorine atoms and methyl and ethoxycarbonyl groups and $R_2$ represents a hydrogen atom, or $R_1$ represents a hydrogen atom and $R_2$ represents a 3-phenoxy group.

It is preferred that $R_1$ represents a chlorine or bromine atom or a trifluoromethyl, trifluoromethoxy, propyl, butoxy, phenyl, 4-chlorophenylthio, 4-chlorophenoxy, 4-methylphenoxy or 4-ethoxycarbonylphenoxy group, especially a chlorine or bromine atom or a trifluoromethyl, trifluoromethoxy, phenyl or 4-chlorophenoxy group.

It is also preferred that $R_2$ represents a hydrogen atom.

A particularly preferred sub-group of compounds is that in which $R_1$ represents a chlorine atom or a phenyl group and $R_2$ represents a hydrogen atom.

Examples of the preparation of acrylic acid morpholide derivatives of formula I are given in EP-A1-0 120 321 and EP-A1-0 219 756.

Examples of systemic, contact and soil fungicides which are particularly suitable for use in a composition according to the present invention are given below:

(A) Systemic fungicides

1. Benalaxyl
2. Cymoxanil
3. Cyprofuram
4. Metalaxyl
5. Ofurace
6. Oxadixyl
7. Fosetyl-aluminium
8. Phosphorous acid and its salts.

(B) Contact fungicides

1. Anilazine
2. Captafol
3. Captan
4. Chlorothalonil
5. Dichlofluanid
6. Dithianon
7. Fentin acetate
8. Folpet
9. Copper
10. Copper oxychloride
11. Mancozeb
12. Maneb
13. Metiram
14. Propineb
15. Zineb

(C) Soil fungicides

1. Etridiazole
2. Fenaminosulf
3. Hymexazol
4. Propamocarb
5. Prothiocarb

The generic names given in groups A, B and C above represent compounds having the following IUPAC names:

Group A

1. Methyl N-phenylacetyl-N-2,6-xylyl-D,L-alaninate.
2. 1-(2-cyano-2-methoxyiminoacetyl)-3-ethylurea.
3. (±)-α-[N-(3-chlorophenyl)cyclopropanecarboxamido]-γ-butyrolactone.
4. Methyl N-(2-methoxyacetyl)-N-(2,6-xylyl)-D,L-alaninate.
5. (±)-α-2-chloro-N-2,6-xylylacetamido-γ-butyrolactone.
6. 2-methoxy-N-(2-oxo-1,3-oxazolidin-3-yl)acet-2′,6′-xylidide.
7. Aluminium tris(ethyl phosphonate).

Group B 1. 4,6-dichloro-N-(2-chlorophenyl)-1,3,5-triazin-2-amine.
2. 1,2,3,6-tetrahydro-N-(1,1,2,2-tetrachloroethylthio)phthalimide.
3. 1,2,3,6-tetrahydro-N-(trichloromethylthio)phthalimide.
4. Tetrachloroisophthalonitrile.
5. N-dichlorofluoromethylthio-N′,N′-dimethyl-N-phenylsulphamide.
6. 2,3-dicyano-1,4-dithia-anthraquinone.
7. Triphenyltin acetate.
8. N-(trichloromethylthio)phthalimide.

10. Dicopper chloride trihydroxide.
11. Manganese ethylenebis(dithiocarbamate) complex with zinc salt.
12. Manganese ethylenebis(dithiocarbamate).
13. Zinc ammoniate ethylenebis(dithiocarbamate)-poly(ethylenethiuram disulphide).
14. Polymeric zinc propylenebis(dithiocarbamate).
15. Zinc ethylenebis(dithiocarbamate).

Group C 1. 5-ethoxy-3-trichloromethyl-1,2,4-thiadiazole.
2. Sodium 4-dimethylaminobenzenediazosulphonate.
3. 5-methylisoxazol-3-ol.
4. Propyl 3-(dimethylamino)propylcarbamate.
5. S-ethyl(3-dimethylaminopropyl)thiocarbamate.

Of the systemic fungicides listed above, cymoxanil, fosetyl-aluminium, phosphorous acid and disodium phosphite are especially preferred and, of the contact fungicides listed above, chlorothalonil, dithianon and mancozeb are especially preferred for use in a composition according to the present invention.

Some formula I compounds may also be combined to advantage with compounds from Group A and Group B in a triple combination.

The improved effect of the compositions according to the present invention is thought to be due to synergism or breakdown of resistance. Another advantage is the broader spectrum of activity.

The compositions according to the invention can be used preventively or curatively in a number of crops such as grapes, potatoes, tomatoes, cucumbers, tobacco, hops, pumpkins, cabbages and other vegetables, rubber, citrus fruits, avocados, pineapples, cocoa, roses, carnations and other ornamental plants.

Combinations between compounds of formula I and compounds from groups A and B are also particularly suitable for the control of fungal diseases in grapes if the vine is already infected (curative treatment).

The quantities of active ingredients used in combined products according to the invention depend on the application rates for the compounds when used on their own, but also on the proportion of one product to another and on the degree of synergism. Also of relevance is the target fungus. The relative proportions between formula I compounds and group A, B and C compounds may in extreme cases be between 1:160 and 60:1 or 50:1 based on parts by weight of active ingredient but are preferably between 1:20 and 10:1.

Specific information on the quantity proportions is given below.

Formula I compounds are applied in concentrations of between 25–1000 ppm, and preferably between 100–500 ppm, whereas the amounts of compounds combined with them should preferably be as follows (all figures in ppm):

| Group A | |
|---|---|
| Compound 1,3,4,5,6: | 20–500 (50–200) |
| Compound 2: | 50–500 (80–150) |
| Compound 7: | 100–2500 |
| Compound 8: | 100–4000 (600–2000) |
| Group B | |
| Compound 1,2,4,5,14: | 400–2000 (500–1500) |
| Compound 3,8: | 800–3000 (100–2000) |
| Compound 6: | 150–700 (250–500) |
| Compound 7: | 250–800 (400–700) |
| Compound 9,10,11,12,13,15: | 1200–3000 (1500–2000) |
| Group C | |
| Substance 1,3: | 300–2000 (500–1500) |
| Substance 2,4,5: | 500–1500 (800–1200) |

A composition according to the invention may further comprise a carrier, the active ingredients being present in a total amount of 0.5 to 95% by weight.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

The compositions according to the invention may be formulated as solutions, emulsions, wettable powders, suspensions, powders, dusts, pastes, soluble powders, granulates, suspension or emulsifiable concentrates or aerosols. Solutions and powders contained in polymer capsules are also suitable, as are natural or synthetic materials or carriers impregnated with the active substance.

These formulations are manufactured in the usual way, such as by mixing the active substances with liquid solvents and/or solid carriers, where appropriate-with the addition of surfactants i.e. emulsifiers and/or dispersants, stabilisers, wetting agents, binding agents, dyes and odorisers. The invention therefore also includes a method for making a fungicidal composition as defined above which comprises bringing the active ingredients into association with at least one carrier.

If water is used as a solvent or diluent, organic solvents may also be used as auxiliary solvents or antifreeze additives. Suitable organic solvents include aromatics such as benzene, xylene, toluene, alkylbenzenes, alkylnaphthalenes and chlorinated aromatics; chlorinated aliphatic hydrocarbons such as chlorobenzene, chloroethylene, trichloroethane, methylene chloride, chloroform, carbon tetrachloride and polychloroethane; aliphatic hydrocarbons such as petroleum fractions, cyclohexane, light mineral oils, paraffins and kerosine; particularly suitable, however, are polar solutions i.e. alcohols such as isopropanol, butanol, glycols, benzyl alcohol, furfuryl alcohols and cyclohexanol as well as their ethers and esters; ketones such as acetone, methyl ethyl ketone, methyl isobutyl ketone, cyclohexanone, -butyrolactone, and also dimethylformamide, dimethyl sulphoxide and N-methyl-pyrrolidone. Mixtures of different liquids are often suitable.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates. In particular, suitable solid carriers for powders or dusts include naturally occurring rock flours, montmorillonite, kieselguhr or diatomite, and synthetic ground minerals such as micro-dispersed silicic acid or aluminium oxide; suitable granulate carriers include broken and graded natural rocks such as lime spar, marble, pumice, sepiolite and dolomite and synthetic granulates made of organic and inorganic flours. In addition, granulates can be made from organic material such as sawdust, coconut shell flour, corncob fibre and dried tobacco stems.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amides or amines containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide. In particular, the following may be used as emulsifiers and/or wetting agents: nonionic emulsifiers such as polyoxyethylene fatty acid esters, polyoxyethylene fatty alcohol ethers, polyoxyethylene fatty amines, ethoxylated castor oil, and anionic emulsifiers such as acidic and neutralised alkylsulphonates, alkyl sulphates and aryl sulphonates. Lignin sulphite lyes and derivatised celluloses may be used as dispersants.

Binding agents such as carboxymethyl alcohol, natural water-soluble polymers such as gum arabic, and synthetic polymers in the form of powders, granules or latex such as polyvinyl alcohol or polyvinyl acetate may be incorporated into the formulations.

The formulations may contain colourants in the form of inorganic pigments such as iron oxide, titanium oxide or prussian blue, or organic dyes such as alizarin, azo-dyes, metallic phthalocyanines or triphenylmethane dyes. They may also contain odorisers e.g. natural perfume oils.

Depending on the type, the formulations preferably contain between 5% and 85% by weight of active substance, preferably 20–80% by weight in solid formulations, 10–50% in formulations where the active substances are in solution and 10–60% by weight where the active substances are in suspension.

Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

Products as described in the invention may be in the form of finished formulations i.e. in which the substances are already combined (see Examples 1 to 11). However, the components of the combinations may also be supplied as separate formulations for mixing in the tank immediately before application (see Examples 12–16). Concentrates according to the invention are generally mixed with water to obtain the desired concentration of active substance.

The composition of the invention may also contain other ingredients, for example other compounds possessing herbicidal, insecticidal or fungicidal properties. It is also possible to mix them with nematicides, bird repellents, growth regulators, plant nutrients or soil conditioners.

Of particular interest in enhancing the duration of the protectant activity of the compounds of this invention is the use of a carrier which will provide a slow release of the fungicidal compounds into the environment of the plant which is to be protected. Such slow-release formulations could, for example, for example, be inserted in the soil adjacent to the roots of a vine plant, or could include an adhesive component enabling them to be applied directly to the stem of a vine plant.

The compositions are applied in the normal way; e.g. by pouring, spraying, misting, dusting or scattering. The quantities to be applied according to the invention may vary depending on weather conditions or the state of the crop. The time to apply may be before or after infection. This is most important as in practice the point at which infection occurred cannot be recognised immediately. The duration of protection is normally dependent on the individual compound selected, and also a variety of external factors, such as climate, whose impact is normally mitigated by the use of a suitable formulation.

The invention still further provides the use as a fungicide of a composition as defined above, and a method for combating fungus at a locus, which comprises treating the locus, which may for example be plants subject to or subjected to fungal attack, seeds of such plants or the medium in which such plants are growing or are to be grown, with such a composition.

The invention is illustrated in the following Examples.

EXAMPLE 1

Emulsifiable concentrate formulation

| | |
|---|---|
| Phosphorous acid | 22.3% by weight |
| β-(4-chlorophenyl)- β-(3,4-dimethoxyphenyl)acrylic acid morpholide | 3.0% by weight |
| sec-butylamine | 9.7% by weight |
| Emulsifier (Na-alkyl benzene sulphonate) | 15% by weight |
| Solvent (cyclohexanone) | 50% by weight |

Phosphorous acid is dissolved in the solvent and then the acrylic acid morpholide is added. This produces a clear, bright yellow solution. The solution stays clear after the sec-butylamine and the emulsifier have been added.

EXAMPLE 2

Wettable powder formulation

| | |
|---|---|
| Fosetyl-aluminium | 50% by weight |
| β-(4-chlorophenyl)-β-(3,4-dimethoxyphenyl)acrylic acid morpholide | 10% by weight |
| Wetting agent (alkylnaphthalene sulphonate) | 2% by weight |
| Dispersant (lignin sulphonate) | 8% by weight |
| Carrier (kaolin) | 30% by weight |

The components (all of which are solid) are mixed together and ground in a pinned disc mill until the particles are reduced to approx. 5–10 μm.

EXAMPLE 3

Wettable powder formulation

| | |
|---|---|
| Disodum phosphite | 50% by weight |
| β-(4-chlorophenyl)-β-(3,4-dimethoxyphenyl)acrylic acid morpholide | 5% by weight |
| Na-diisooctyl-sulpho-succinate (wetting agent) | 2% by weight |
| Sodium sulphate (dispersant) | 10% by weight |
| Lignin sulphonate (dispersant) | 8% by weight |
| Kaolin (carrier) | 25% by weight |

$Na_2HPO_3$ is produced by neutralising $H_3PO_3$ with NaOH in aqueous solution and then spray drying.

The components are mixed thoroughly and ground in a pinned disc mill.

EXAMPLE 4

Emulsifiable concentrate formulation

| | |
|---|---|
| Phosphorous acid | 20% by weight |
| β-(4-biphenylyl)-β-(3,4-dimethoxyphenyl)-acrylic acid morpholide | 5% by weight |
| Emulsifier (ethoxylated triglyceride) | 15% by weight |
| Solvent (diethylene glycol dimethyl ether) | 60% by weight |

The phosporous acid is dissolved in the solvent and then the acrylic acid morpholide and the emulsifier are added. A clear solution is produced.

EXAMPLE 5

Wettable powder formulation

| | |
|---|---|
| Mancozeb (85%) | 63% by weight |
| β-(3,4-dimethoxyphenyl)-β-(4-biphenylyl)-acrylic acid morpholide | 10% by weight |
| Sodium sulphate | 5% by weight |
| Kaolin (carrier) | 12% by weight |
| Alkyl naphthalene sulphonate (wetting agent) | 2% by weight |
| Lignin sulphonate (dispersant) | 8% by weight |

The ingredients are mixed and ground in a pinned disc mill.

EXAMPLE 6

Suspension-emulsion concentrate formulation

| | |
|---|---|
| β-(4-biphenylyl)-β-(3,4-dimethoxyphenyl)-acrylic acid morpholide | 3% by weight |
| Mancozeb (85%) | 15% by weight |
| Lauryl alcohol polyglycol ether phosphate (emulsifier 1) | 4% by weight |
| Ethoxylated triglyceride (emulsifier 2) | 2% by weight |
| Dodecyl benzene sulphonic acid, Ca-salt (emulsifier 3) | 1.5% by weight |
| Ethylene oxide propylene oxide copolymer (dispersant) | 2.5% by weight |
| Cyclohexanone | 35% by weight |
| Alkyl aromatic fraction (boiling point >200° C.) | 37% by weight |

The acrylic acid morpholide is dissolved in 80% of the solvent, then the emulsifiers and the dispersants are added and the mixture is stirred throughly. After the Mancozeb is added, the mixture is ground in a bead mill (1 mm glass beads) and then the rest of the solvent is added.

EXAMPLE 7

Aqueous suspension formulation

| | |
|---|---|
| β-(4-biphenylyl)-β-(3,4-dimethoxyphenyl)-acrylic acid morpholide | 15% by weight |
| Dithianon (95%) | 25% by weight |
| Dispersant (alkyl naphthalene sulphonate) | 2% by weight |
| Stabiliser (hemicellulose) | 1% by weight |
| Antifreeze (propylene glycol) | 5% by weight |
| Water | 52% by weight |

The acrylic acid morpholide and the dithianon are ground in a bead mill (1 mm glass beads) together with 80% of the water and the dispersant. The other components are dissolved in the rest of the water and then stirred into the other ingredients.

EXAMPLE 8

Wettable powder formulation

| | |
|---|---|
| β-[4-(4-chlorophenoxy)phenyl]-β-(3,4-dimethoxyphenyl)-acrylic acid morpholide | 5% by weight |
| Chlorothalonil min (95%) | 40% by weight |
| Wetting agent (alkyl naphthalene sulphonate) | 2% by weight |
| Carrier material (kieselguhr) | 20% by weight |
| Dispersant (lignin sulphonate) | 8% by weight |
| Filler (chalk) | 25% by weight |

The acrylic acid morpholide is dissolved in acetone, and the solution is applied to the carrier. The carrier is evaporated, the other ingredients are crushed and added, and the mixture is ground in a pinned disc mill.

EXAMPLE 10

The formulation in example 1 is tested biologically in a glass house in comparison with a 10% emulsifiable concentrate of β-(4-chlorophenyl)-β-(3,4-dimethoxyphenyl)-acrylic acid morpholide (I') and with phosphorous acid.

Test plants: grapevine seedlings at the 3-leaf stage (glass house)
Infection: plasmopara viticola
Application: 2 days after infection A range of dosage rate concentrations was selected which would allow proper observation of the increase in effect.

| Active substance | Effect in % with a dosage rate in ppm of: | | | | |
|---|---|---|---|---|---|
| | 100 | 747 | 50 | 374 | 25 | 188 |
| I' | 51 | | 58 | | 30 | |
| phosphorous acid | | 6 | | 8 | | 0 |
| Combination of both substances | 81 | | 70 | | 43 | |

EXAMPLE 11

Effect against plasmopara viticola

The active substances I' and fosetyl-aluminum were tested separately and in combination in the same way as in example 10.

| Active substance | Dosage in ppm to achieve an effect of: | |
|---|---|---|
| | 50% | 80% |
| I' | 100 | >>100 |
| Fosetyl-aluminum | >>1000 | >>1000 |
| I' + fosetyl-aluminum | 25 | 100 |
| | 185 | 747 |

Whilst 100 ppm I' only had a 50% effect and much more than 1000 ppm were required for the same effect with fosetyl-aluminum, a 50% effect was achieved by combining 25 ppm I' and 188 ppm fosetyl: 100 ppm I' and 747 ppm fosetyl-aluminum gave an effect of 80%.

EXAMPLE 12

Effect on pseudoperonospora cubensis

I' and dithianon were tested separately and in combination for their effect against pseudoperonospora cubensis on open grown cucumbers. Four sprayings were carried out at 7-day intervals.

| Active substance | Dosage rate (ppm) required to achieve an effect of: | | |
|---|---|---|---|
| | 50% | 72% | 80% |
| I' | 250 | 800 | >800 |
| Dithianon | 400 | >750 | >750 |
| I' + dithianon | 100 375 | 300 375 | |

EXAMPLE 13

Effect on phytophthora infestans

I' and Mancozeb were tested separately and together (tank mixture) for their effect on phytophthora infestans in potatoes. Assessment was made 4 weeks after final treatment. The table shows the effect in % when certain concentrations of active substance were used.

| ppm | 0 | 800 | 1100 | 1600 (Mancozeb) |
|---|---|---|---|---|
| 0 | 0 | 11 | 24 | 47 |
| 100 | 0 | 18 | 48 | 49 |
| 150 | 0 | 24 | 53 | 57 |
| 200 (I') | 0 | 23 | 51 | 63 |

Whilst I' had no effect at the given dosages of 100, 150 and 200 ppm, the effect of 1600 ppm Mancozeb was increased to 63% when 200 ppm I' was added to it.

EXAMPLE 14

Effect on phytophthora infestans

The test described in example 13 was also carried out with β-(3,4-dimethoxyphenyl)-β(4-biphenylyl)-acrylic acid-morpholide (I") and Mancozeb. The results are given in the following table:

| ppm | 0 | 1100 | 1600 (Mancozeb) |
|---|---|---|---|
| 0 | 0 | 24 | 47 |
| 50 | 0 | 41 | 48 |
| 100 | 0 | 50 | 68 |
| 300 (I") | 2 | 79 | 85 |

Again, there is clear evidence of synergism.

EXAMPLE 15

Effect against Plasmopara viticola

The active compounds β-(4-chlorophenyl)-β-(3,4-dimethoxyphenyl)-acrylic acid morpholide (I') and fosetyl-aluminum were tested singly as well as their combination.

| Compound | Concentration | Efficiency |
|---|---|---|
| I' | 100 ppm | 58.1% |
| fosetyl-aluminum | 750 ppm | 8.8% |
| | 1000 ppm | 8.1% |
| I' + | 100 ppm | |

-continued

| Compound | Concentration | Efficiency |
| --- | --- | --- |
| fosetyl-aluminum | 750 ppm | 84.4% |
| I' + | 100 ppm | |
| fosetyl-aluminum | 1000 ppm | 86.9% |

EXAMPLE 16

Effect against Plasmopara viticola

The active compounds β-(4-chlorophenyl)-β-(3,4-dimethoxyphenyl)-acrylic acid morpholide (I') and cymoxanil were tested singly as well as their combination.

| Compound | Concentration | Efficiency |
| --- | --- | --- |
| I' | 80 ppm | 35.0% |
| Cymoxanil | 80 ppm | 7.5% |
| I' + | 80 ppm | |
| Cymoxanil | | 58.8% |

NB. In Examples 15 and 16, % efficiency indicates the percentage of uninfected leaves.

We claim:

1. A fungicidal composition comprising a contact fungicide comprising a manganese ethylenebis(dithiocarbamate) complex with zinc salt and at least one acrylic acid morpholide derivative of the formula

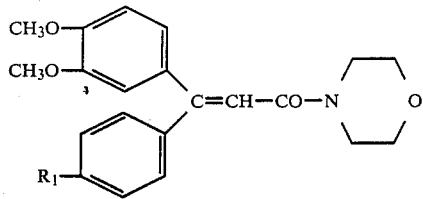

in which $R_1$ represents a chlorine atom or a phenyl group, the weight ratio of acrylic acid morpholide derivative to said contact fungicide within said composition being in the range of from 1:32 to 1:4, based on parts by weight of active ingredient.

2. The composition of claim 1 further comprising a carrier.

3. The composition of claim 2 further comprising at least two carriers, at least one of which is a surface-active agent.

4. The composition of claim 1 wherein $R_1$ comprises chlorine.

5. The composition of claim 1 wherein $R_1$ comprises phenyl.

6. A method of combating fungus at a locus which comprises treating the locus with a fungicidally effective amount of the composition according to claim 1.

7. A method of combating fungus at a locus which comprises treating the locus with a fungicidally effective amount of the composition according to claim 4.

8. A method of combating fungus at a locus which comprises treating the locus with a fungicidally effective amount of the composition according to claim 5.

9. The method of claim 6, wherein said locus comprises plants subject to or subjected to fungal attack, seeds of such plants or the medium in which the plants are growing or are to be grown.

* * * * *

UNITED STATES PATENT AND TRADEMARK OFFICE
CERTIFICATE OF CORRECTION

PATENT NO. : 4,923,866
DATED : May 8, 1990
INVENTOR(S) : GUIDO ALBERT ET AL.

It is certified that error appears in the above-indentified patent and that said Letters Patent is hereby corrected as shown below:

On the cover page of the patent, the inventors should be corrected to read as follows:

--Guido Albert, Hackenheim, Jurgen Curtze, Geisenheim-Johannisberg, Edmund Friedrichs, Ingelheim am Rheim, all of Fed. Rep. of Germany--.

Signed and Sealed this

Sixth Day of January, 1998

Attest:

BRUCE LEHMAN

Attesting Officer

Commissioner of Patents and Trademarks